United States Patent [19]  [11] 4,110,342
Bigham  [45] Aug. 29, 1978

[54] AZIDOMETHYLARYLACETIC ACIDS AND ESTERS THEREOF

[75] Inventor: Eric C. Bigham, Waterford, Conn.

[73] Assignee: Pfizer Inc., New York, N.Y.

[21] Appl. No.: 833,906

[22] Filed: Sep. 16, 1977

[51] Int. Cl.$^2$ ..................... C07D 333/24; A01N 9/00
[52] U.S. Cl. ............................. 260/332.2 A; 424/275
[58] Field of Search ................................. 260/332.2 A

[56] References Cited
PUBLICATIONS

Chem. Abstracts, vol. 13, p 9932a.

Primary Examiner—A. Siegel
Attorney, Agent, or Firm—Connolly and Hutz

[57] ABSTRACT

Azidomethylarylacetic acids and derivatives thereof are prepared by oxidative rearrangement of the corresponding azidomethylarylmethyl ketones effected by thallium (III) nitrate in the presence of methanol or ethanol and certain acids to obtain methyl or ethyl esters of the desired azidomethylarylacetate. When desired, the acids are obtained by hydrolysis of said esters. The azidomethylarylacetic acids are valuable intermediates in the preparation of aminomethylarylmethylpenicillins and aminomethylarylmethylcephalosporins.

4 Claims, No Drawings

AZIDOMETHYLARYLACETIC ACIDS AND ESTERS THEREOF

BACKGROUND OF THE INVENTION

1. Field of the Invention

This invention relates to a novel process for preparing azidomethylthienylacetic acids and certain esters thereof useful in the synthesis of aminomethylthienylmethylpenicillins and aminomethylthienylmethylcephalosporins. The novel azidomethylthienylacetic acids are prepared by oxidative rearrangement of azidomethylthienylmethyl ketones by thallium (III) nitrate in the presence of methanol or ethanol and certain specified acids to provide the methyl azidomethylthienylacetates when methanol is employed or the corresponding ethyl esters when ethanol is used. The azidomethylthienylacetic acids are obtained by hydrolysis of the esters. The azidomethyl compounds provided by the process of the invention are useful intermediates in the preparation of aminomethylthienylmethylpenicillins and -cephalosporins by acylation of 6-APA, 7-ACA or their derivatives to obtain corresponding azidomethylthienylmethyl compounds which are then converted to the analogous aminomethyl compounds by well-known means. British Pat. No. 1,467,407 (Derwent No. 73775V) discloses a similar process employing amino-protected methyl 5-aminomethyl-2-thienyl ketones to provide the corresponding 2-thienylacetic acids. However, the use of methyl azidomethylthienyl ketones is novel and unexpected in view of the prior art which discloses that alkyl azides are unstable to acids such as those employed in the present process.

2. Description of the Prior Art

McKillop et al., *J. Am. Chem. Soc.*, 93, 4919 (1971) has shown that thallium (III) nitrate in methanol containing perchloric acid converts acetophenones into methyl phenylacetates. However, in defining the limitations of this conversion the author points out that the reaction is unsuccessful when applied to compounds containing an amino group due to preferential complexation of the amino substituent with the thallium electrophile. The corresponding amides are stated to react normally. The above-mentioned British Pat. No. 1,467,407 discloses that amino protected 5-aminomethyl-2-thienylacetic acids may be prepared by reaction of amino protected 2-acetyl-5-aminomethylthiophenes with thallium (III) nitrate in the presence of lower alkanols such as methanol and perchloric acid followed by hydrolysis of the intermediate ester. The use of the amino protected 5-aminomethyl-2-thienylacetatic acids or a reactive functional derivative thereof to acylate certain 7-aminocephalosporanic acids and derivatives thereof followed by removal of the amino protecting group to provide the corresponding 7-(5-aminomethyl-2-thienylmethyl)cephalosporins is also described.

U.S. Pat. Nos. 3,966,710 and 3,997,527 disclose a series of aminomethylarylmethylpenicillins, particularly 6-(phenyl- and thienylacetamido)penicillanic acids and esters substituted in the phenyl and thienyl moieties with an aminomethyl substituent. The aminomethylarylacetic acid intermediates employed, including 2-aminomethyl-3-thienylacetic acid and 3-aminomethyl-2-thienylacetic acid were prepared by conventional synthetic methods. The former compound was prepared from 2-aminomethyl-3-methylthiophene by acetylation, free radical catalyzed bromination to obtain N-acetyl-2-aminomethyl-3-bromomethylthiophene; this intermediate was then converted to the 3-cyanomethyl analog which was hydrolyzed to the desired 3-thienylacetic acid. The isomeric 3-aminomethyl-2-thienylacetic acid was obtained from 2-thienylacetamide via the corresponding N-hydroxymethyl compound, cyclization to 3-aminomethyl-2-thienylacetic acid lactam and hydrolysis.

The amino moiety of the aminomethyl substituted arylacetic acids was protected, preferably by reaction with methyl acetoacetate as taught in U.S. Pat. No. 3,813,376, prior to acylation of 6-APA or its esters.

o-Azidomethylphenylacetic acid and methods for its preparation from o-bromomethylphenylacetate esters are disclosed in U.S. Pat. Nos. 3,766,175; 3,813,391; 3,814,755 and 3,840,535. However, the azidomethylthienylacetic acids and esters are not known in the art.

Abramovitch and Kyba in "The Chemistry of the Azido Group", S. Patai, Editor, Interscience Publishing Co., New York, 1971, Chapter 5, pp. 221–239, record that alkyl azides, including aralkyl azides, are unstable in the presence of protonic acids such as sulfuric, hydrochloric, perchloric and trifluoroacetic acids, especially upon warming. Such azides are also reported to be unstable to Lewis acids such as aluminum trichloride and antimony pentachloride.

SUMMARY OF THE INVENTION

It has now been found that novel compounds of the formula:

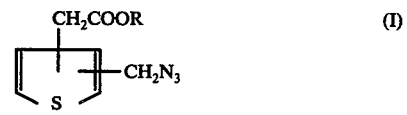

wherein R is hydrogen or $R^O$ where $R^O$ is methyl or ethyl are obtained by a novel process which comprises the steps of:

(a) contacting approximately equimolar amounts of a ketone of the formula:

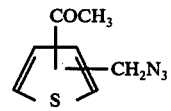

and thallium (III) nitrate in the presence of at least a molar excess of an alcohol of the formula $R_OOH$ and from about 0.1 to 10 moles of acid per mole of said ketone, said acid being a member selected from the group consisting of perchloric, sulfuric, nitric, toluenesulfonic, methanesulfonic, fluosulfonic and fluoboric acids, at a temperature of from about 0° to 80° C. to obtain a product of formula (I) wherein R is said $R_O$; and (b) hydrolyzing said product of step (a) under ester hydrolyzing conditions when a compound of formula (I) wherein R is hydrogen is desired.

The process of the invention is unexpected in view of the prior art which teaches that organic azides such as the above azidomethyl group containing reactants and products of the process are unstable to the strong acids employed. The products provided have advantages over aminomethylthienylacetic acids as intermediates in the synthesis of aminomethylthienylmethylpenicillins and -cephalosporins since the azido containing acids or certain carboxyl derivatives thereof known in the art for acylation of penicillins and cephalosporins may be employed directly without protection of the azido group to provide the corresponding azidomethylthienylmethylpenicillins and cephalosporins, and the azido group subsequently converted to an amino group by simple catalytic hydrogenation. The use of aminomethylthienylacetic acid, on the other hand, requires the use of an amino protecting group and subsequent removal thereof from the penicillin or cephalosporin precursor.

It is a further object of this invention to provide the novel compounds of formula (I), especially 2-azidomethyl-3-thienylacetic acid, 3-azidomethyl-2-thienylacetic acid, 5-azidomethyl-2-thienylacetic acid and the methyl and ethyl esters of each.

DETAILED DESCRIPTION OF THE INVENTION

The process of the present invention may be employed to prepare azidomethylarylacetic acids and derivatives thereof of the general formula

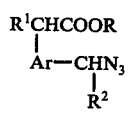

wherein R is hydrogen or $R^o$ where $R^o$ is methyl or ethyl; $R^1$ is hydrogen, methyl or ethyl; $R^2$ is hydrogen or alkyl having from one to three carbon atoms; and Ar is

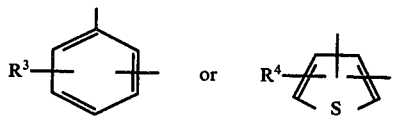

wherein $R^3$ is a member selected from the group consisting of hydrogen, F, Cl, Br, hydroxy and alkoxy having from one to three carbon atoms; and $R^4$ is a member selected from the group consisting of hydrogen, F, Cl and Br; which comprises contacting approximately equimolar amounts of a ketone of the formula

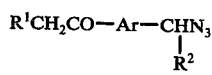

and thallium (III) nitrate in the presence of an alcohol, $R^oOH$ and in the presence of certain strong acids.

Particularly preferred, however, is the process for the production of the novel azidomethylthienylacetic acids and esters of the formula

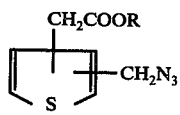

wherein R is as defined above.

In carrying out the preferred process the appropriate methyl azidomethylthienyl ketone and thallium (III) nitrate are contacted in the presence of methanol or ethanol which has been acidified with certain strong acids. By "strong acid" within the context of this invention is meant an organic or inorganic acid having a pKa of about 2 or lower. Suitable strong acids are those that allow the desired reaction to take place without substantial production of undesirable by-products. While many such suitable strong acids are available in the art, preferred such acids are perchloric, sulfuric, nitric, toluenesulfonic, methanesulfonic, fluosulfonic and fluoboric acids. An especially preferred acid is perchloric acid for reasons of economy and efficiency.

The above-mentioned ketone starting material and thallium (III) nitrate are preferably contacted in equimolar amounts. However, a molar excess of either reactant may be employed if desired. While the amount of alcohol theoretically required is also equimolar, it is preferable to use at least a molar excess of said alcohol, up to about 100 moles per mole of said ketone, such that the alcohol also serves as a solvent for the reaction.

The mole ratio of the preferred strong acid to said ketone may vary over a wide range from about 0.01 to 100 moles of such acid per mole of said ketone. A preferred range of such acid, however, is from about 0.1 to 10 moles per mole of ketone and an especially preferred range is from about 3 to 5 moles of such acid per mole of said ketone.

The preferred range of temperature for the process of Step (a) is from about 0° to 80° C. At temperatures substantially lower than 0° C. the reaction rate is exceedingly slow. Temperatures above about 80° C. for the reaction require the use of pressure equipment and such high temperatures cause excessive amounts of undesirable by-products to be formed. Of course, as one skilled in the art is aware, within the preferred range of temperature the reaction will proceed faster at higher temperatures and more slowly at lower temperatures. Within the preferred range of temperature the reaction ordinarily is substantially complete in from about 0.5 to 50 hours. A particularly preferred temperature is room temperature, i.e., from about 15° to 30° C., at which temperature the reaction is substantially complete within about 2 to 24 hours.

The process of the invention is illustrated by the following reaction sequence employing methyl 2-azidomethyl-3-thienyl ketone and methanol.

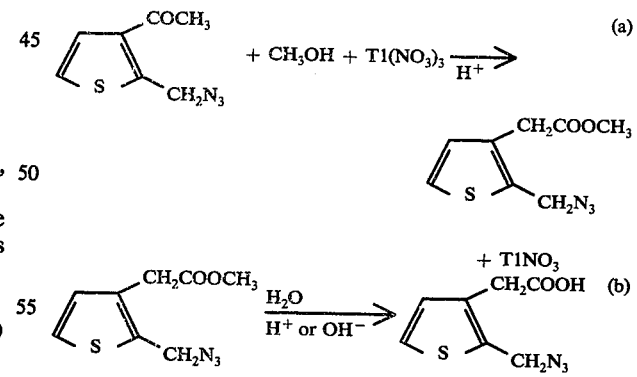

Thallium (I) nitrate precipitates from the reaction mixture as a white solid during the reaction. When the reaction of Step (a) is substantially complete the desired azidomethylthienylacetic acid ester is isolated by standard methods well known in the art. For example, the reaction mixture may be filtered to remove precipitated salt, the filtrate concentrated, diluted with water and concentrated again to ensure complete removal of alcohol. The residue is partitioned between water and a water immiscible solvent such as, for example, ethyl ether, chloroform or benzene, and the organic extracts are washed, dried and evaporated to dryness. The crude residual ester may be used in Step (b) or may be further purified, for example by recrystallization or by column chromatography.

The methyl and ethyl esters provided in Step (a) serve as intermediates which are converted to the desired azidomethylthienylacetic acids by hydrolysis in Step (b). The hydrolysis may be carried out under either alkaline or acidic conditions commonly used in the art for ester hydrolysis. When alkaline conditions are employed, the ester is contacted with aqueous base optionally in the presence of a water miscible organic solvent such as ethanol, methanol or acetone. Examples of bases which may be employed are sodium hydroxide, potassium carbonate and calcium hydroxide. The alkaline hydrolysis may be allowed to proceed at room temperature or may be heated at temperatures up to the reflux temperature. The resulting alkali metal or alkaline earth salt of the azidomethylthienylacetate is acidified and the acid isolated by standard means well known in the art.

When acid hydrolysis is employed, it is preferred that the ester obtained in Step (a) is dissolved in a water miscible organic solvent such as, for example ethanol, methanol, acetone, dimethoxyethane, diethylene glycol dimethyl ether or tetrahydrofuran. An especially preferred such solvent is tetrahydrofuran. To this solution is added an aqueous solution of an acid. While any of the acids ordinarily employed for ester hydrolysis will suffice, preferred such acids are sulfuric, phosphoric and hydrochloric acid. Hydrochloric acid is especially preferred for reasons of efficiency. The acidic hydrolysis is preferably carried out at a temperature in the range of from about room temperature up to the reflux temperature of the solvent. Reflux temperature is particularly preferred to shorten the time required for hydrolysis to about 2 to 8 hours.

When the acid hydrolysis is substantially complete, the reaction mixture is cooled and the desired acid isolated by standard methods well known in the art. For example, the reaction mixture is made alkaline with, e.g., sodium hydroxide or potassium carbonate, the alkaline mixture washed with ether to remove neutral organic material, the aqueous layer acidified and re-extracted with ether. The ether extracts are then evaporated to provide the desired azidomethylthienylacetic acid which is of suitable purity for use in acylation of penicillins or cephalosporins. If desired, however, the azidomethylthienylacetic acid may be further purified by standard means such as by column chromatography.

As will be obvious to one skilled in the art, the acidic reaction mixture from Step (a) may be used in Step (b), after separation of precipitated thallium (I) nitrate, without isolation of the ester. For example, the alcoholic filtrate from the Step (a) reaction mixture may be diluted with water and hydrolyzed as described above either with or without addition of one of the acids preferred for hydrolysis.

The azidomethylthienylacetic acids of the invention or the reactive functional carboxyl derivatives thereof may be used to acylate 6-aminopenicillanic acid (6-APA), its esters, including monosilyl and disilyl-6-APA and other derivatives of 6-aminopenam such as, for example, 6-amino-2,2-dimethyl-3-(tetrazol-5-yl)penam which is disclosed in U.S. Pat. No. 4,026,881 and Belgian Pat. No. 821,163. The acids of formula (I) can likewise be used to acylate 7-aminocephalosporanic acids such as, for example, those of British Pat. No. 1,467,407; U.S. Pat. Nos. 3,766,175; 3,766,176 and 3,814,755, as well as other 7-aminocephem derivatives, for example the 4-(tetrazol-5-yl)-3-cephems of U.S. Pat. No. 3,966,719.

The acylation methods which may be used to provide the above-mentioned azidomethylthienylacetamidopenams and -cephems are well known in the art. For example, the free acids of formula (I) may be employed directly for acylation of the above mentioned 6-aminopenams and 7-aminocephems, in which case a suitable condensing agent, e.g., N,N'-dicyclohexylcarbodiimide, is also employed; or the acid of formula (I) may first be converted into a reactive functional carboxyl derivative, e.g., the acid chloride, acid bromide or mixed anhydride with the ethyl half-ester of carbonic acid which is then condensed with the 6-aminopenam or 7-aminocephem. These and other well known acylation methods which may be employed are described in, e.g., U.S. Pat. Nos. 3,966,719; 4,024,249; Belgian Pat. No. 821,163; British Pat. No. 1,467,407 and Ekstrom et al., *Acta. Chem. Scand.,* 19, 281–299 (1965).

While the azidomethylthienylacetamidopenicillins and corresponding cephalosporins are themselves valuable antibacterial agents, they preferably serve as intermediates to provide the more potent antibacterial aminomethylthienylacetamidopenicillins and cephalosporins such as, for example, those disclosed in U.S. Pat. No. 4,009,160 and British Pat. No. 1,467,407. The azido group is conveniently converted to an amino group by catalytic hydrogenation, while the hydrogenation may be carried out employing any of the catalysts and conditions known to those skilled in the art, it is preferred to employ a palladium catalyst. The palladium catalyst may be supported on, for example, activated carbon or calcium carbonate or may be unsupported palladium powder or palladium formed in situ by reaction of a palladium oxide or salt with hydrogen.

The hydrogenation may be carried out under a wide range of temperature and pressure conditions. However, temperatures in the range of about 0° to 100° C. and especially about 25° to 50° C. are preferred. Preferred pressures for the hydrogenation are from about atmospheric pressure to 5 atmospheres. The hydrogenation is carried out in the presence of a reaction-inert solvent such as, for example, water, ethanol, methanol, tetrahydrofuran, dioxane or mixtures thereof. Ordinarily, the azidomethyl group containing compound dissolved in said solvent is mixed with catalyst, adjusted to a pH of about 6–8 and hydrogenated in a suitable apparatus well known to those skilled in the art. When hydrogen uptake is substantially complete, the catalyst is removed by filtration and the desired aminomethylthienylacetamidopenicillin or -cephalosporin isolated by standard methods, such as, for example, precipitation at the isoelectric point or acidification and extraction into a suitable water immiscible solvent, for example, chloroform or ethyl ether. The isolated antibacterial compound may be purified, if desired, for example, by column chromatography.

Preparation of Starting Materials

2-Acetyl-3-methylthiophene and 2-acetyl-4-methylthiophene are prepared by acetylation of commercially-available 3-methylthiophene with acetic anhydride in the presence of phosphoric acid by the procedure of Hartough and Kosak, *J. Am. Chem. Soc.,* 69, 3093 (1974). Using the same procedure with commercial 2-methylthiophene provides 2-acetyl-5-methylthiophene.

3-Acetyl-2-methylthiophene is obtained by acetylation of 2-thenyl-magnesium chloride by the method of Gaertner, J. Am. Chem. Soc., 73, 3934 (1951). 3-Acetyl-4-methylthiophene is provided by the following reaction sequence:

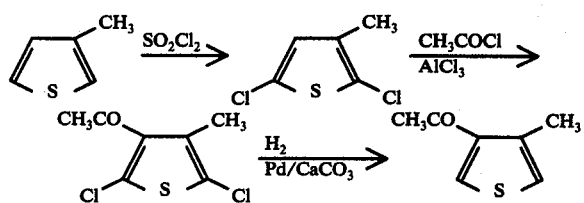

The chlorination step is carried out by the method of Campaigne and LeSuer, J. Am. Chem. Soc., 71, 333 (1949). The acetylation step is carried out in a hydrocarbon solvent in an inert atmosphere. The dehalogenation to provide the desired intermediate is carried out employing a palladium-on-calcium carbonate catalyst by well-known means; see, for example, Freifelder, "Practical Catalytic Hydrogenation", John Wiley and Sons, Inc., New York, 1971.

4-Acetyl-2-methylthiophene is prepared by the reaction of 2-methylthiophene-4-carboxylic acid [Shvedov et al., Khim. Geterotsikl. Soedin., 1010 (1967); Chem. Abstr., 69, 51922j (1968)] with methyl lithium or by reacting the corresponding acid chloride with lithium dimethylcopper or dimethyl cadmium. The acetyl methylthiophenes are converted to the requisite azidomethylthienylmethyl ketones as outlined below for 3-azidomethyl-2-thienylmethyl ketone.

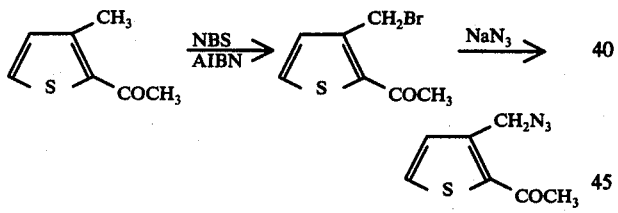

The thienyl bromides are obtained by reacting equimolar amounts of the acetyl methylthiophene and N-bromosuccinimide (NBS) and a catalytic amount of α,α-azobisisobutyronitrile (AIBN) in carbon tetrachloride. The mixture is heated at reflux, typically for about 4 hours, and worked up by methods well known to those skilled in the art. The thenyl bromides obtained are reacted with an equimolar amount of sodium azide in aqueous acetone. This step is ordinarily carried out at room temperature for about 2 to 4 hours and the desired product isolated by standard procedures well known in the art.

The following examples are provided to further illustrate the invention. However, they are not to be construed as limitations of this invention, many variations of which are possible without departing from the spirit or scope thereof. In the examples the following abbreviations are used: $^1$H NMR for Proton Nuclear Magnetic Resonance Spectra, s for singlet, d for doublet, q for quartet, IR for infrared.

EXAMPLE 1

Methyl 3-Azidomethyl-2-thienylacetate

To a solution of methyl 3-azidomethyl-2-thienyl ketone (20.5 g., 0.113 mole) in 230 ml. of methanol and 46 ml. of 70% aqueous perchloric acid, was added 55.1 g. (0.124 mole) thallium (III) nitrate trihydrate. A white precipitate of thallium (I) salts soon formed. The resulting mixture was stirred at 20°-25° C. for 24 hours. Sodium chloride, 10.5 g., was added, the suspension stirred for 15 minutes and then filtered. The filtrate was evaporated in vacuo to about half volume, 150 ml. of water was added and the solution evaporated again to remove the remaining methanol. The resulting mixture was diluted with water and extracted three times with 200 ml. portions of diethyl ether. The combined extracts were washed with saturated sodium chloride solution, saturated sodium bicarbonate solution till basic, dried over magnesium sulfate and evaporated to dryness. The residue was filtered through a 1-inch layer of Florisil, washing with chloroform, and the filtrate evaporated to obtain the desired product as an oil, 17.2 g. (72% yield). $^1$H—NMR (CDCl$_3$), ppm. ($\delta$): 7.22 (d, J=5, aromatic-H), 7.0 (d, J=5, aromatic-H), 4.35 (s, CH$_2$N$_3$), 3.8 (s, CH$_2$), 3.7 (s, OCH$_3$); IR spectrum (film), cm.$^{-1}$: 3100, 2100 (N$_3$), 1740 (CO$_2$CH$_3$).

EXAMPLE 2

Ethyl 3-Azidomethyl-2-thienylacetate

When an equal volume of ethanol is employed to replace the methanol used in Example 1 and the reaction mixture is heated at reflux for 1 hour then worked up as described in Example 1, the title compound is obtained.

When the above reaction in ethanol is carried out at 0° C. for 3 days the results are substantially the same.

EXAMPLE 3

Methyl 5-Azidomethyl-2-thienylacetate

When the procedure of Example 1 was repeated but employing an equivalent amount of 5-azidomethyl-2-thienylmethyl ketone in place of the 3-azidomethyl isomer used therein, the title compound was obtained as an oil in 53% yield. $^1$H—NMR (CDCl$_3$), ppm. ($\delta$): 7.6–6.8 (m, aromatic-H), 4.50 (s, CH$_2$), 3.85 (s, CH$_2$), 3.75 (s, OCH$_3$); IR spectrum (film), cm.$^{-1}$: 2950, 2100, 1740, 1450.

EXAMPLE 4

Ethyl 2-Azidomethyl-3-thienylacetate

Methyl 2-azidomethyl-3-thienyl ketone (18.1 g., 0.10 mole) is dissolved in a mixture of 180 ml. of ethanol and 1.0 g. (0.01 mole) of concentrated sulfuric acid. Thallium (III) nitrate trihydrate (44.4 g., 0.10 mole) is added and the mixture is heated at reflux for three hours and allowed to stand overnight at room temperature. The precipitated salt is removed by filtration, the filtrate concentrated in vacuo to a small volume, 125 ml. of water added and the solution again evaporated to a small volume. The resulting residue is partitioned between water and ethyl ether, and the combined ether extracts washed with saturated brine, then saturated sodium bicarbonate solution and dried over magnesium sulfate. The crude title compound is obtained upon evaporation of solvent. Further purification, when desired, is obtained by chromatography on Florisil or Sephadex LH-20.

EXAMPLE 5

When the procedure of Example 4 is repeated, but employing the acid catalyst, reaction temperature and times indicated below, ethyl 2-azidomethyl-3-thienylacetate is similarly obtained.

| Acid Catalyst | Mole Ratio Acid Cat./ketone | Reaction Temp. °C. | Time, Hrs. |
| --- | --- | --- | --- |
| $H_2SO_4$ | 5 | 50 | 8 |
| $HClO_4$ | 10 | 15 | 24 |
| p-Toluenesulfonic acid, hydrate | 3 | 80 | 1 |
| $CH_3SO_3H$ | 10 | 80 | 0.5 |
| $FSO_3H$ | 1 | 25 | 30 |
| $HBF_4$ | 0.1 | 30 | 50 |
| $HNO_3$ | 5 | 0 | 50 |

EXAMPLE 6

Methyl 2-Azidomethyl-4-thienylacetate

Methyl 2-azidomethyl-4-thienyl ketone (9.05 g., 0.05 mole), 150 ml. of methanol, 12.0 g. (0.15 mole) of 70% nitric acid and 22.2 g. (0.05 mole) of thallium (III) nitrate trihydrate is heated at reflux for 2 hours, cooled to room temperature, neutralized with dilute sodium hydroxide solution, filtered and the filtrate worked-up as described in Example 4 to obtain the title compound.

EXAMPLE 7

Methyl 4-Azidomethyl-2-thienylacetate

When the procedure of Example 1 is repeated, but employing methyl 4-azidomethyl-2-thienyl ketone as starting material in place of the methyl 3-azidomethyl-2-thienyl ketone used therein, the title compound is obtained in like manner.

EXAMPLE 8

Methyl 4-Azidomethyl-3-thienylacetate

When the procedure of Example 1 is repeated but employing methyl 4-azidomethyl-3-thienyl ketone as starting material in place of the methyl 3-azidomethyl-2-thienyl ketone used therein, the title compound is similarly obtained.

EXAMPLE 9

3-Azidomethyl-2-thienylacetic Acid

Methyl 3-azidomethyl-2-thienylacetate (15.6 g., 0.074 mole) was dissolved in 200 ml. of tetrahydrofuran and 30 ml. of 3M hydrochloric acid was added. The solution was heated at reflux for 5 hours, then cooled and adjusted to pH 10 with 10% (by weight) sodium hydroxide solution. The alkaline mixture was washed with 3 × 250 ml. of diethyl ether, the aqueous layer adjusted to pH 2 and extracted with 3 × 250 ml. of the same solvent. The combined ether extracts were dried and evaporated to dryness to obtain 10.5 g. (72% yield) of the desired acid as a solid. $^1H$—NMR ($CDCl_3$), ppm. ($\delta$): 9.35 (broad singlet, $CO_2H$), 7.15 (d, J=5, 2 aromatic-H), 4.35 (s, $CH_2N_3$), 3.85 (s, $CH_2CO_2$—); IR spectrum ($CHCl_3$), cm.$^{-1}$: 2100, 1700, 1400, 1250, 860, 700.

Hydrolysis of ethyl 3-azidomethyl-2-thienylacetate by the above procedure or by employing an equal volume of 6M sulfuric acid or 8M phosphoric acid in place of the 3M hydrochloric acid also affords the title compound.

When 0.05 mole of methyl 3-azidomethyl-2-thienylacetate is refluxed for two hours in a mixture of 200 ml. of methanol and 15 ml. of 5N sodium hydroxide, then 100 ml. of water added, the alcohol evaporated in vacuo, the residue acidified and extracted with ether, 3-azidomethyl-2-thienylacetic acid is similarly obtained.

EXAMPLE 10

5-Azidomethyl-2-thienylacetic Acid

Methyl 5-azidomethyl-2-thienylacetate (21.1 g., 0.10 mole) was dissolved in 300 ml. of tetrahydrofuran and 40 ml. of 3M hydrochloric acid was added. After heating at reflux for 6 hours the reaction mixture was cooled and the product isolated as described in Example 9 to obtain a 62% yield of oil. $^1H$—NMR ($CDCl_3$), ppm. ($\delta$): 9.0 (s, COOH), 6.85 (s, 2 aromatic-H), 4.4 (s, $CH_2N_3$), 3.75 (s, $\underline{CH_2}COO$); IR spectrum (neat, cm.$^{-1}$: 3000 (broad), 2100 ($N_3$), 1710 ($CO_2H$), 1680 and 1475.

EXAMPLE 11

Hydrolysis of the methyl and ethyl esters provided in Examples 4 to 8 under the conditions indicated below in each case similarly provides the following azidomethylthienylacetic acids.

| Product | Solvent* | Acid Catalyst | Temp., °C. | Time, Hrs. |
| --- | --- | --- | --- | --- |
| 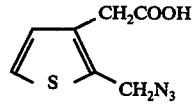 | THF | 6M HCl | 50 | 8 |
| 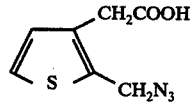 | ethanol | 2M $H_2SO_4$ | 78 | 4 |
| 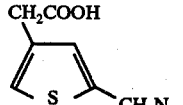 | $CH_3OCH_2CH_2OCH_3$ | 5M $H_3PO_4$ | 82 | 3 |
| 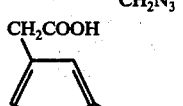 | methanol | 6M $H_2SO_4$ | 50 | 18 |

-continued

| Product | Solvent* | Acid Catalyst | Temp., ° C. | Time, Hrs. |
| --- | --- | --- | --- | --- |
| 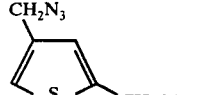 | THF | 3M HCl | 65 | 6 |
| 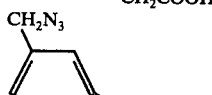 | Diglyme | 3M H₂SO₄ | 100 | 2 |
| 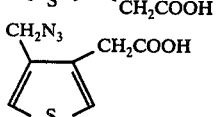 | THF | 6M HCl | 65 | 2 |

*THF is tetrahydrofuran; Diglyme is diethylene glycol dimethyl ether.

EXAMPLE 12
6-(3-Azidomethyl-2-thienylacetamido)penicillanic Acid

6-Aminopenicillanic acid (4.93 g., 0.023 mole) was dissolved in a mixture of 100 ml. each of water and tetrahydrofuran, adjusted to pH 7.5 with 10% aqueous sodium hydroxide solution and cooled to 0° C. At this temperature was added 3-azidomethyl-2-thienylacetic acid (4.5 g., 0.023 mole) followed by 4.4 g. (0.023 mole) of 1-ethyl-3-(3-diemthylaminopropyl)carbodiimide hydrochloride. The pH of the mixture was adjusted to 5.8 and maintained at 0° to 5° C., pH 6.0-6.1 for 3 hours, adding 3N hydrochloric acid as required. The tetrahydrofuran was removed by evaporation in vacuo, the aqueous residue adjusted to pH 8 and washed with ethyl acetate. The aqueous phase was acidified (pH 2.0) and extracted with 3 × 50 ml. of ethyl acetate. The combined extracts were dried over sodium sulfate and evaporated in vacuo to obtain 5.7 g. (63%) of the title compound as a foamed solid; $^1$H—NMR (CDCl$_3$), ppm ($\delta$): 7.8 (d, NH), 7.1 (q, 2 aromatic-H), 3.8 (s, CH$_2$), 1.5 [2s, C(CH$_3$)$_2$]; IR spectrum (KBr), cm$^{-1}$: 2105 (N$_3$), 1786 ($\beta$-lactam). The compound was found to have an in vitro minimum inhibitory concentration (MIC) vs. Step. pyogenes 1.56 µg./ml.

EXAMPLE 13
6-(3-Aminomethyl-2-thienylacetamido)penicillanic Acid 6-(3-Azidomethyl-2-thienylacetamido)penicillanic acid, 1.97 g., was dissolved in 3 ml. of dioxane and 100 ml. of water was added. To the resulting aqueous solution, 0.8 g. of 10% palladium on carbon catalyst was added, the mixture adjusted to pH 6 and hydrogenated with shaking at 45 p.s.i. (3.16 kg./cm$^2$). At 15 minute intervals the mixture was adjusted to pH 6 with 3N hydrochloric acid. When hydrogen uptake was complete the catalyst was removed by filtration, the filtrate adjusted to pH 5.5 and freeze-dried to obtain 1.48 g. (80%) of the desired product. A portion was purified by column chromatography on Sephadex LH-20, eluting with distilled water; M.P. 195°-215° C. (dec.); $^1$H—NMR (D$_2$O) 7.4 (q, 2-aromatic H), 5.5 (m, 2H, 5 and 6 position), 4.3 (s, CH$_2$), 4.0 (s, CH$_2$), 1.65 (s, CH$_3$), 1.5 (s, CH$_3$); IR spectrum (KBr), cm$^{-1}$: 1786, 1666, 1600; in vitro minimum inhibitory concentration (MIC) vs. Strep. pyogenes ≦0.1 µg./ml.

PREPARATION A
Acetyl Thenylbromides i. Methyl 3-Bromomethyl-2-thienyl ketone A mixture of methyl 3-methyl-2-thienylketone (14 g., 0.10 mole), N-bromosuccinimide (18 g., 0.10 mole), α,α-azobisisobutyronitrile (AIBN, 0.3 g.), and carbon tetrachloride (300 ml.) was heated cautiously to reflux under a nitrogen atmosphere. After stirring 4 hours at reflux, the mixture was cooled, filtered to remove succinimide, washed first with sodium bicarbonate solution, then with saturated sodium chloride solution and dried over anhydrous magnesium sulfate. The solvent was evaporated at reduced pressure to obtain a pale yellow solid which was recrystallized from hexane to obtain 16 g. (73%) of the desired product as colorless crystals, M.P. 62°-64° C. $^1$H—NMR (CDCl$_3$), ppm. ($\delta$): 7.5 (d, J=5, aromatic-H), 7.2 (d, J=5, aromatic-H), 4.9 (s, CH$_2$Br) and 2.55 (s, CH$_3$). This compound is a strong irritant.

ii. Methyl 5-Bromomethyl-2-thienyl ketone

Employing methyl 5-methyl-2-thienylketone as starting material in the above procedure provided the title compound in 70% yield, M.P. 58°-59° C. $^1$H—NMR(CDCl$_3$), ppm ($\delta$): 7.5 (d, J=4, aromatic-H), 7.1 (d, J=4, aromatic-H), 4.65 (s, CH$_2$Br), 2.55 (s, CH$_3$).

iii.

Employing the appropriate acetylmethylthiophene in the above procedure the following compounds are similarly obtained:

methyl 2-bromomethyl-3-thienyl ketone
methyl 2-bromomethyl-4-thienyl ketone
methyl 4-bromomethyl-2-thienyl ketone
methyl 4-bromomethyl-3-thienyl ketone.

PREPARATION B
Methyl Azidomethylthienyl Ketones i. Methyl 3-Azidomethyl-2-thienyl Ketone To a solution of methyl 3-bromomethyl-2-thienyl ketone (5 g., 0.023 mole) in 42 ml. of acetone and 4 ml. of water was added sodium azide (1.56 g., 0.024 mole) with caution (exothermic!). The resulting solution was stirred at room temperature for 2.5 hours, the acetone evaporated, the residue diluted with water and extracted with diethyl ether. The combined extracts were washed with water, saturated sodium bicarbonate solution and saturated sodium chloride solution, dried over magnesium sulfate and the dried extracts evaporated to dryness to obtain 4.0 g. (97%) of yellow oil. $^1$H—NMR (CDCl$_3$), ppm. ($\delta$): 7.5 (d, J=5, aromatic-H), 7.2 (d, J=5, aromatic-H), 4.75 (s, CH$_2$N$_3$), 2.5 (s, CH$_3$); IR spectrum (film, cm.$^{-1}$: 3100, 2100 (N$_3$), 1660, 1525 and 1420.

ii. Methyl 5-Azidomethyl-2-thienyl Ketone

Employing methyl 5-bromomethyl-2-thienyl ketone as starting material in the above procedure, the title compound was obtained in 94% yield as an amorphous solid. $^1$H—NMR (CDCl$_3$), ppm. ($\delta$): 7.6 (d, J=4, aromatic-H), 7.1 (d, J=4, aromatic-H), 4.6 (s, CH$_2$), 2.5 (s, CH$_3$CO); IR spectrum (CHCl$_3$), (cm$^{-1}$): 3000, 2975, 2870, 2100, 1675, 1460 and 1370.

iii.

Employing the appropriate methyl bromomethylthienyl ketone selected from those provided in Preparation A, part iii, the following compounds are obtained in a like manner:

methyl 2-azidomethyl-3-thienyl ketone
methyl 2-azidomethyl-4-thienyl ketone
methyl 4-azidomethyl-2-thienyl ketone
methyl 4-azidomethyl-3-thienyl ketone.

PREPARATION C

Methyl-4-methyl-3-thienyl Ketone i. Methyl 2,5-Dichloro-4-methyl-3-thienyl Ketone To a solution of 56.6 g. (0.315 mole) 2,5-dichloro-3-methylthiophene [prepared by the method of Campaigne and LeSeur, J. Am. Chem. Soc., 71, 333 (1949)] and 43.6 ml. (0.614 mole) of acetyl chloride in 165 ml. of petroleum ether under a nitrogen atmosphere was added 48 g. (0.36 mole) of anhydrous aluminum chloride. The mixture was stirred overnight at room temperature, then poured onto ice and extracted with ethyl ether. The combined organic layers were dried, evaporated to dryness and distilled at reduced pressure to yield 49 g. (74%) of the dichloroketone, boiling at 74°–78° C. (0.1 mm.); $^1$H—NMR (CDCl$_3$), ppm. ($\delta$): 2.6 (s, CH$_3$), 2.25 (s, CH$_3$CO).

ii.

A solution of 26.4 g. (0.126 mole) of methyl 2,5-dichloro-4-methyl-3-thienyl ketone in 180 ml. of ethanol is mixed with 5 grams of 10% palladium-on-calcium carbonate and hydrogenated at 3–4 atmospheres hydrogen pressure in a Parr hydrogenation apparatus until hydrogen uptake is complete. The catalyst and salts are removed by filtration and the filtrate evaporated to dryness in vacuo to obtain the title compound.

PREPARATION D

Methyl 2-Methyl-4-thienyl Ketone

2-Methylthiophene-4-carboxylic acid (14.2 g., 0.1 mole) prepared by the method of Shvedov et al., Khim. Geterotsikl. Soedin. 1010 (1967); Chem. Abstrs., 69, 51922j (1968) in 250 ml. of ethyl ether is cooled to −10° to 0° C. and an ethereal solution of methyl lithium (4.4 g., 0.2 mole) is added dropwise while maintaining the reaction mixture below 0° C. After stirring for 1 hour at 0° C., a solution of 4 g. of water in 100 ml. of ethanol is added cautiously and the mixture allowed to warm to room temperature. The desired product is then isolated by partitioning the reaction mixture between ether and water and evaporation of the organic extracts.

What is claimed is:

1. A compound of the formula

[structure: thiophene ring with CH$_2$COOR and CH$_2$N$_3$ substituents] (I)

wherein R is hydrogen or R$^O$ where R$^O$ is methyl or ethyl.

2. A compound according to claim 1 of the formula

[structure: thiophene with CH$_2$COOR and CH$_2$N$_3$]

3. A compound according to claim 1 of the formula

[structure: thiophene with CH$_2$N$_3$ and CH$_2$COOR]

4. A compound according to claim 1 of the formula

[structure: thiophene with N$_3$CH$_2$ and CH$_2$COOR]

* * * * *